US00PP11261P

United States Patent [19]

Theobald

[11] Patent Number: Plant 11,261

[45] Date of Patent: Mar. 7, 2000

[54] BIDENS PLANT NAMED 'INNBID'

[75] Inventor: Hendrik Theobald, Heidesheim, Germany

[73] Assignee: InnovaPlant GmbH + Co. KG, Gensingen, Germany

[21] Appl. No.: 09/004,811

[22] Filed: Jan. 9, 1998

[51] Int. Cl.[7] ..... A01H 5/00

[52] U.S. Cl. ..... Plt./263

[58] Field of Search ..... Plt./263

[56] References Cited

PUBLICATIONS

GTITM UPOVROM Citation for 'InnBid' as per AU PBR96285, Dec. 23, 1996.

*Primary Examiner*—Howard J. Locker
*Assistant Examiner*—Kent L. Bell
*Attorney, Agent, or Firm*—C. A. Whealy

[57] ABSTRACT

A distinct cultivar of Bidens plant named 'Innbid', characterized by its uniform, compact, and freely branching growth habit; spherical plant shape; moderately vigorous growth rate; numerous inflorescences with bright yellow ray florets; and excellent garden and outdoor performance.

1 Drawing Sheet

The present invention relates to a new and distinct cultivar of Bidens plant, botanically known as *Bidens ferulifolia,* and hereinafter referred to by the cultivar name 'Innbid'. The new cultivar is being marketed under the name 'Goldie'.

The new Bidens was discovered by the inventor in a controlled environment in Gensingen, Germany, in June, 1995, as a naturally-occurring mutation of the nonpatented *Bidens ferulifolia* 'Goldmarie'. The new Bidens was observed as a single plant in a large population of plants of the parent cultivar. In side-by-side comparisons conducted in Gensingen, Germany, plants of the new Bidens differed from plants of the cultivar 'Goldmarie' in the following characteristics:

1. Plants of the new Bidens are more uniform, compact, denser and less vigorous than plants of the cultivar 'Goldmarie'.
2. Plants of the new Bidens have shorter internodes than plants of the cultivar 'Goldmarie'.
3. Plants of the new Bidens have, darker green, smaller, broader and more overlapping leaflets than plants of the cultivar 'Goldmarie'.
4. Inflorescences of plants of the new Bidens are smaller and have more rounded and brighter yellow ray florets than inflorescences of plants of the cultivar 'Goldmarie'.
5. Inflorescences of plants of the new Bidens are closer to the foliage than inflorescences of planst of the cultivar 'Goldmarie'.

Asexual reproduction of the new cultivar by terminal cuttings taken in Gensingen, Germany, has shown that the unique features of this new Bidens are stable and reproduced true to type in successive propagations.

The cultivar 'Innbid' has not been observed under all possible environmental conditions. The phenotype may vary somewhat with variations in environment such as temperature, light intensity, and fertility level, without, however, any variance in genotype.

The following traits have been repeatedly observed and are determined to be the unique characteristics of 'Innbid '. These characteristics in combination distinguish 'Innbid' as a new distinct cultivar:

1. Uniform and compact growth habit.
2. Initially upright then outwardly spreading plant shape; eventually becoming roughly spherical.
3. Freely branching, bushy, and dense; suitable for hanging basket containers.

4. Moderately vigorous growth rate.
5. Numerous inflorescences with bright yellow ray florets that last for a long period of time.
6. Excellent garden and outdoor performance.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of a typical hanging basket plant of the cultivar 'Innbid'.

The photograph at the bottom of the sheet comprises a close-up view of typical leaves and inflorescences of a plant of the cultivar 'Innbid'.

Inflorescence and foliage colors in the photographs may appear different than the actual colors due to light reflectance.

DETAILED BOTANICAL DESCRIPTION

The following observations and measurements describe plants grown during the spring and summer in Encinitas, Calif., under full sun with day and night temperatures averaging 24° and 16° C., respectively. Color references are made to The Royal Horticultural Society Colour Chart except where general terms of ordinary dictionary significance are used.

Botanical classification: *Bidens ferulifolia* cultivar 'Innbid'.

Parentage: Naturally-occurring mutation of *Bidens ferulifolia* cultivar 'Goldmarie' (not patented).

Progagation:

*Type.*—By cuttings and by tissue culture.

*Time to initiate roots.*—Summer: About 10 days at temperatures of 22° C. Winter: About 15 days at temperature of 22° C.

*Time to develop roots.*—Summer: About 15 days at temperatures of 22° C. Winter: About 20 days at temperatures of 22° C.

*Rooting habit.*—Vigorous and fibrous.

Plant description:

*Form.*—Herbaceous annual in temperate regions. Initially upright then outwardly spreading; eventually becoming roughly spherical. Suitable for hanging basket containers.

*Branching habit.*—Freely branching, very dense and bushy. Removal of terminal apices enhances branching.

*Plant height.*—About 18 cm.

*Plant diameter.*—About 54 cm.

*Vigor.*—Moderate.

*Lateral stem description.*—Internode length: About 1.5 cm. Diameter: About 2.5 mm. Texture: Short, fine white hairs. Color. Young: Close to 186B. Mature, woody: 174A.

*Foliage description.*—Leaves pinnatifid, opposite and generally symmetrical. Leaflets overlapping. Foliage durable. Length: About 2.25 cm. Width: About 1.75 cm. Shape: Pinnatifid, acute apex and cuneate base. Texture: Slight pubescence on lower surface, densest on petiole. Color: Young leaves, upper surface: 146A/147A. Young leaves, lower surface: 147B. Mature leaves, upper surface: 147A. Mature leaves, lower surface: 147B. Venation, upper surface: 147A. Venation, lower surface: 147B. Petiole: Length: About 6 mm. Diameter: About 1 mm. Color: Reddish, 186A/186B.

Inflorescence description:

*Inflorescence type and habit.*—Single star-shaped daisy-type composite inflorescece form. Ray and disc florets arranged acropetally on a capitulum. Inflorescences persistent. Inflorescences flat and orientated perpendicular to stem.

*Quantity of inflorescences.*—Freely flowering with numerous inflorescences per plant. One inflorescence per terminal apex.

*Natural flowering season.*—Natural flowering season is spring through autumn. Plants flower continuously during this period. Inflorescences last about 10 days.

*Fragrance.*—Not detected.

*Inflorescence diameter.*—About 2.75 cm.

*Inflorescence depth (height).*—About 9 mm.

*Ray Florets.*—Appearance: Smooth, satiny, longitudinally ribbed. Quantity: Usually five per inflorescence. Shape: Ovate to oblong. Apex: Tri-dentate. Margin: Entire. Length: About 1.2 cm. Width: About 6.5 mm. Color. When opening, upper surface: Brighter than 9A. When opening, lower surface: 9A/9B. Mature, upper surface: Brighter than 9A, floret color does not fade. Mature, lower surface: 9A/9B.

*Disc florets.*—Shape: Cylindrical. Quantity: About 20 per inflorescence. Disc floret length: About 7.5 mm. Disc floret width: About 1 mm. Color: 154A at base, 14A at apex.

*Phyllaries.*—Shape: Ovate with rounded to acute apex. Quantity: Typically seven per inflorescence with five smaller, narrower, acuminate, pale green bractlets interior to phyllaries. Margin: Entire. Length: About 5.5 mm. Width: About 2.7 mm.

*Peduncle.*—Length: About 4 cm. Strength: Wiry and flexible but strong. Color: 144A.

*Inflorescence bud.*—Shape: Cup-shaped. Length: About 3 mm. Diameter: About 3 mm.

*Androecium.*—Present on disc florets only. Anther color: 14A. Pollen color: 14A. Amount of pollen: Moderate.

*Gynoecium.*—Present on ray and disc florets.

Disease resistance: The new Bidens has not been observed to be more resistant to pathogens common to Bidens.

Seed production: Seed production has not been observed.

It is claimed:

1. A new and distinct cultivar of Bidens plant named 'Innbid', as illustrated and described.

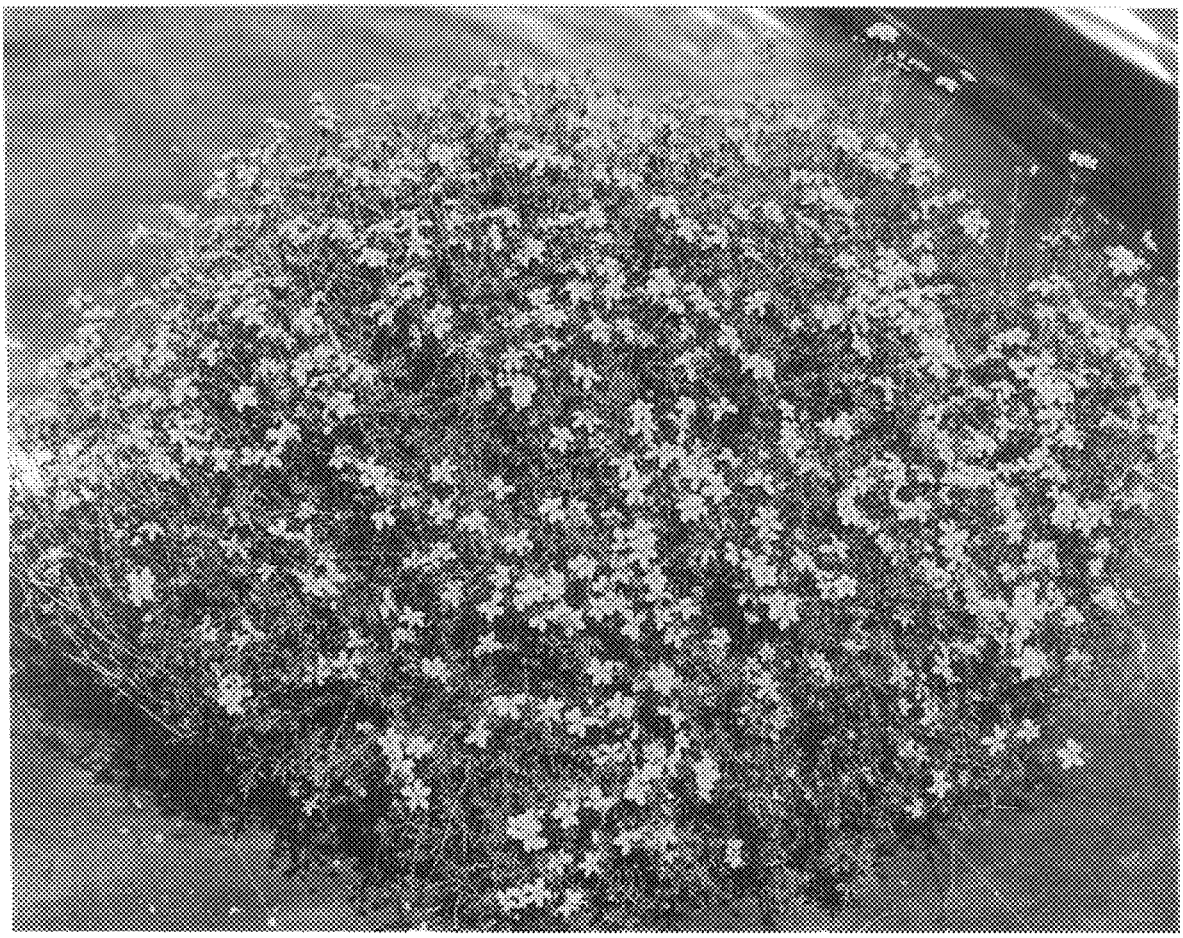
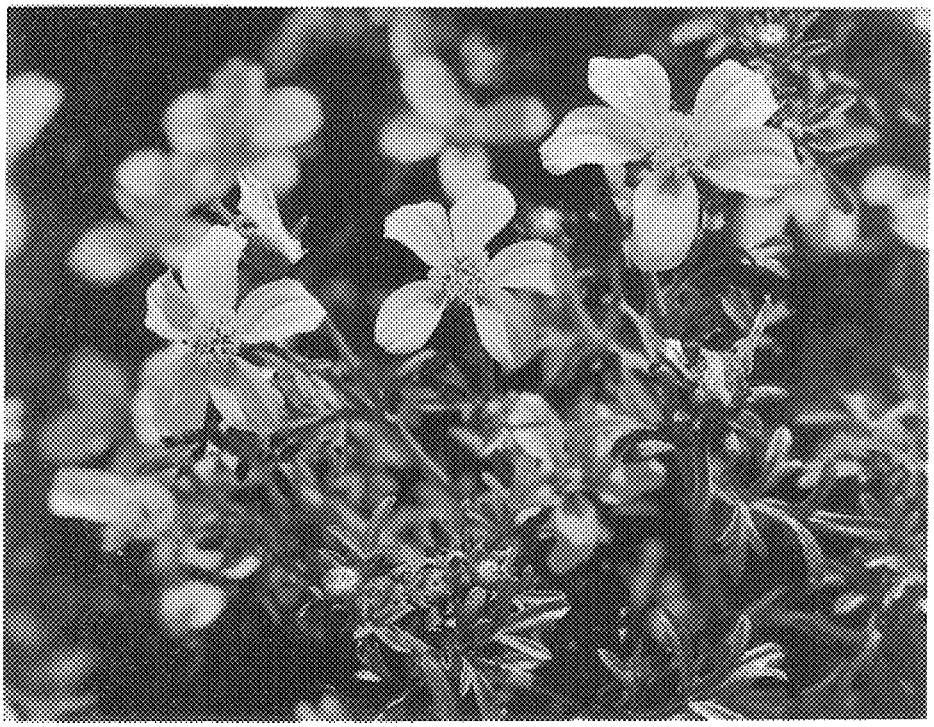

* * * * *